United States Patent

Fujita et al.

[11] 4,014,700
[45] Mar. 29, 1977

[54] FURAN CONTAINING AZO DYE DEVELOPERS

[75] Inventors: Shinsaku Fujita; Yukio Maekawa; Kazuya Sano; Seiki Sakanoue, all of Minami-ashigara, Japan

[73] Assignee: Fuji Photo Film Co., Ltd., Minami-ashigara, Japan

[22] Filed: Nov. 22, 1974

[21] Appl. No.: 526,188

[30] Foreign Application Priority Data

Nov. 22, 1973 Japan .................. 48-131494

[52] U.S. Cl. .................. 96/73; 96/3; 96/29 D; 96/77; 96/99
[51] Int. Cl.[2] .................. G03C 7/00; G03C 1/40; G03C 1/76; G03C 1/10
[58] Field of Search .................. 96/77, 3, 29 D, 73, 96/99

[56] References Cited

UNITED STATES PATENTS

| | | | |
|---|---|---|---|
| 3,134,672 | 5/1964 | Blout et al. | 96/3 |
| 3,307,947 | 3/1967 | Idelson et al. | 96/3 |
| 3,579,334 | 5/1971 | Cieciuch et al. | 96/3 |

*Primary Examiner*—David Klein
*Assistant Examiner*—Richard L. Schilling
*Attorney, Agent, or Firm*—Sughrue, Rothwell, Mion, Zinn & Macpeak

[57] ABSTRACT

A yellow dye developer having improved photographic properties represented by the formula (I)

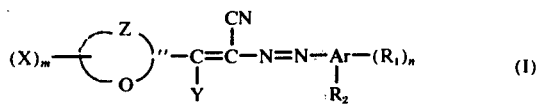

wherein X represents a hydrogen atom, a halogen atom, a nitro group, a hydroxyl group, an alkyl group having 1 to 4 carbon atoms, an acylamino group having 1 to 4 carbon atoms; Z represents an atomic group necessary for completing a furan ring or a benzofuran ring; Y represents a hydroxyl group, an acyloxy group having 1 to 4 carbon atoms, or an alkoxyacyloxy group having 2 to 4 carbon atoms; Ar represents an aromatic ring; $R_1$ represents a hydrogen atom, a halogen atom, an acyl group having 1 to 4 carbon atoms, or an alkyl group having 1 to 5 carbon atoms; $R_2$ represents a hydroxyl group, an acyloxy group having 1 to 4 carbon atoms, or an alkoxyacyloxy group having 2 to 4 carbon atoms with the $R_2$ group being at the ortho-position to the azo group; $m$ and $n$ each is an integer of 1 to 4; and at least one of X, Z, Ar and $R_1$ being bonded to a polyhydric phenol moiety directly or through an atom or a divalent group; and a photographic material containing the dye developer.

12 Claims, 5 Drawing Figures

FURAN CONTAINING AZO DYE DEVELOPERS

BACKGROUND OF THE INVENTION

1. Field of the Invention

The present invention relates to photography and more particularly it relates to dye developers used for photographic materials which provide images by the diffusion transfer process.

An object of the present invention is to provide dye developers, the spectral absorption characteristics of which are modified to effect a temporary hypsochromic shift in the wave lengths absorbed during exposure of an associated photosensitive emulsion and which, subsequent to exposure, can be restored to their original absorption characteristics.

Another object of the present invention is to provide novel photographic processes whereby temporarily shifted dye developers, that is, dye developers the spectral absorption bands of which have been temporarily shifted to lower wave lengths prior to exposure of a photosensitive element containing the dye developers, can be restored to their original spectral absorption characteristics subsequent to exposure of the photosensitive element.

2. Description of the Prior Art

A color image forming method employing the dye transfer process using dye developers is disclosed in the specification of U.S. Pat. Nos. 2,983,606; 3,134,764; 3,188,209; 3,255,001; 3,316,090; and 3,345,163. A dye developer is a compound having a group capable of developing an exposed silver halide emulsion and a dye portion and is a compound which is immobilized depending on the amount of the silver halide developed, with the remaining portion of the dye developer being transferred into an image-receiving element to provide a transferred image.

When such a dye developer is disposed at the exposure side of a silver halide photosensitive emulsion layer, with which the dye developer is associated, having substantially a spectral sensitivity in the spectral absorption region of the dye developer or is incorporated in the silver halide photosensitive layer, the silver halide emulsion is desensitized in appearance by the light absorption of the dye developer itself. To prevent desensitization, a method is proposed as described in the specification of U.S. Pat. Nos. 3,307,947 and 3,579,334 in which a dye developer is initially chemically converted into a compound having absorption in a shorter wave length region and then is restored to the original compound having the original absorption by reaction with a processing composition during development. However, the aforesaid patent discloses only magenta dye developers. Also, the same idea as described above is achieved for yellow dye developers in the specification of U.S. Pat. No. 3,230,085 but since the dye developers disclosed in this patent form at the same time a carboxylic acid due to the action of the alkali in the processing composition, the immobilization of the quinone moiety of the dye developer formed as the result of the development of silver is insufficient. Thus, it is difficult to avoid the occurence of the so-called "leakage", that is the occurence of certain transfer of the dye at the bright portion of the color image.

Yellow dye developers used for diffusion transfer photography are must satisfy the following criteria (1) the absorption of the dye after transfer is preferably yellow, (2) the dye has good solubility in a solvent for the dispersion of the dye in a photographic emulsion, and (3) the dye has good transfer efficiency and no transfer at the bright portion of a color image occurs. Also, a temporary short wave type dye developer must satisfy, in addition to the aforesaid criteria, the criteria that (4) the absorption of the dye developer, the absorption of which has been temporarily shifted to a short wave length side, is disposed at a sufficiently shorter wave length region, so that it does not obstruct the sensitivity of the silver halide emulsion, (5) recoloring occurs quickly due to the action of a processing composition, and (6) recoloring does not occur during the storage of the photographic material (i.e., the dye developer is stable).

The "temporary shift of the absorption region of such a dye developer to a shorter wave length side" is ordinarily attained by acylating the hydroxyl group or the amino group thereof which is an auxochrome of an azo dye. It is believed that since an azo dye can assume two tautomeric forms, i.e., a hydrazono-type tautomer having a long wave length absorption and an azo-type tautomer having a short wave length absorption, the absorption region of the azo dye can be shifted to a shorter wave length side by fixing the azo dye in the azo-type tautomer by acylation of the dye. On the other hand, few examples of such yellow azo dyes satisfing the aforesaid six criteria are known in the art; that is, in regard to, for instance, a pyrazolone azo dye, a 3-acrylazo-2,4-dihydroxyquinoline dye, a 2-arylazo-1,3-indadione, etc., the acylation thereof is utterly impossible or quite difficult; in regard to, for instance, a pyrazolobenzimidazole azo dye and a pyrimidazoloazo dye, the degree of shift of the absorption region of the dye to a shorter wave length side by the acylation of the dye is insufficient; and in regard to, for instance, an aniline-type azo dye, the acylated azo dye is not recolored by the action of a developing composition.

Furthermore, although the compounds described in the specification of U.S. patent application Ser. No. 486,730 filed July 8, 1974 may satisfy the aforesaid criteria, these compounds have insufficient solubility and transfer efficiency in using them for diffusion transfer photographic materials. Also, with respect to the hue of the image after transfer, the dye has an absorption at a slightly shorter wave length region than the absorption region of a desirable yellow dye, which requires improvement.

SUMMARY OF THE INVENTION

Therefore, an object of this invention is to provide excellent and novel yellow dye developers which satisfy the above described criteria (1) to (3).

A further object of this invention is to provide dye developers whose absorption can be temporarily shifted to a shorter wave length satisfying the above-described criteria (4) to (6) in addition to criteria (1) to (3) of the above-described yellow dye developers.

It has now been discovered that the compounds represented by the following general formula (I) satisfy the above-described objects of this invention;

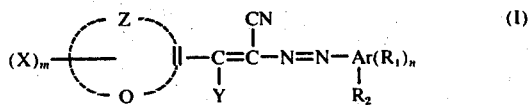

wherein X represents a hydrogen atom, a halogen atom, a nitro group, a hydroxyl group, an alkyl group having 1 to 4 carbon atoms, or an acylamino group having 1 to 4 carbon atoms; Z represents an atomic group necessary for completing a furan ring or a benzofuran ring; Y represents a hydroxyl group; an acyloxy group having 1 to 4 carbon atoms, or an alkoxyacyloxy group having 2 to 4 carbon atoms; Ar represents an aromatic ring; $R_1$ represents a hydrogen atom, a halogen atom, an acyl group having 1 to 4 carbon atoms, or an alkyl group having 1 to 5 carbon atoms; $R_2$ represents a hydroxyl group, an acyloxy group having 1 to 4 carbon atoms, or an alkoxyacyloxy group having 2 to 4 carbon atoms with $R_2$ being at the ortho position to the azo group; m and n each represents an integer of 1 to 4; and at least one of X, Z, Ar and $R_1$ being bonded, either directly or through an atom or a divalent group, to a polyhydric phenol moiety having a silver halide developing action.

DETAILED DESCRIPTION OF THE INVENTION

Figure 1:
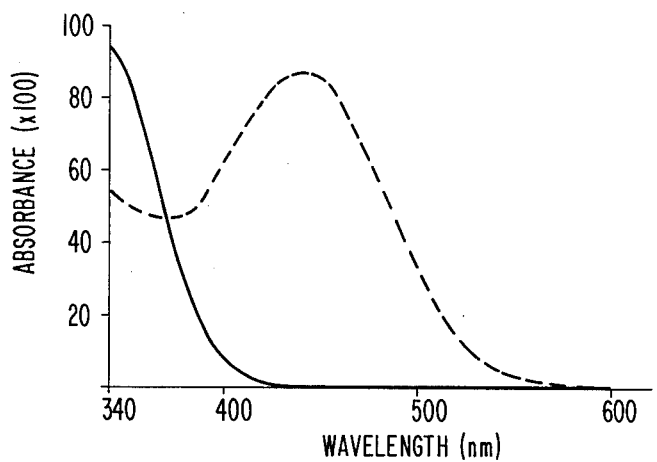
FIG. 1 shows the spectral absorption of Dye Developer 1 (solid line) in ethanol and that of Comparative Dye Developer 1 (dotted line) after addition of one drop of a 1 N sodium hydroxide solution and neutralization with acetic acid.

As described above, a feature of the present invention is using the dye developers represented by the above-described general formula (I), in which X represents a hydrogen atom; a halogen atom, e.g., a chlorine atom, a bromine atom, etc.; a nitro group; a hydroxyl group; an alkyl group having 1 to 4 carbon atoms such as a methyl group, an ethyl group, a propyl group, an isopropyl group, a butyl group, a sec-butyl group, a t-butyl group, etc.; or an acylamino group having 1 to 4 carbon atoms such as an acetylamino group, a propionylamino group, a butyrylamino group; Z represents an atomic group necessary for completing a furan ring or a benzofuran ring; Y represents a hydroxyl group; an acyloxy group having 1 to 4 carbon atoms such as an acetyloxy group, a propionyloxy group, a butyryloxy group, etc.; or an alkoxyacyloxy group having 2 to 4 carbon atoms such as a methoxyacetyloxy group, etc.; Ar represents an aromatic ring such as a benzene ring, a naphthalene ring, etc.; $R_1$ represents a hydrogen atom; a halogen atom such as a chlorine atom, a bromine atom, etc.; an acyl group having 1 to 4 carbon atoms such as an acetyl group, a propionyl group, a butyryl group, etc.; or an alkyl group having 1 to 5 carbon atoms such as a methyl group, an ethyl group, a propyl group, an isopropyl group, a butyl group, an isobutyl group, a sec-butyl group, a t-butyl group, a sec-amyl group, a t-amyl group, etc.; $R_2$ represents the following specified groups positioned as a substituent at the ortho-position to the azo group, that is, a hydroxyl group; an acyloxy group having 1 to 4 carbon atoms such as an acetyloxy group, a propionyloxy group, a butyryloxy group, etc.; or an alkoxyacyloxy group having 2 to 4 carbon atoms such as a methoxyacetyloxy group; and $m$ and $n$ each represents an integer of 1 to 4; at least one of X, Z, Ar and $R_1$ being bonded to a polyhydric phenol having developing action (such as, preferably a hydroquinonyl group, a 2,5-dihydroxyphenyl group, an ortho-dihydroxyphenyl group, or an acylated group thereof, e.g., an acetylated group and a propionylated group thereof capable of being converted into the above group in an alkaline solution) directly or through an atom or a divalent group such as —S—, —NHCO—, $-(CH_2)_p-$ S $-(CH_2)_q-$ wherein p and q each represents 0 or a positive integer and $p + q$ is less than 6, $-(CH_2)_p-SO_2-(CH_2)_q-$ where p and q have the same meaning as above, and an alkylene group containing 1 to 6 carbon atoms, preferably $-(CH_2)_r-$ where r is an integer of 1 to 6.

The dye developers used in this invention will be explained in greater detail hereinbelow.

When the dye developer is a benzofuran ring type compound, the dye provides a more preferable hue of the dye image after transfer but the transfer efficiency is a slightly reduced as the molecular weight of the dye increases. The substituent at the condensed benzene ring does not greatly influence the hue. When the furan ring is substituted with a thiophene ring, the hue shifts to a shorter wave length side. As Y and Z groups, an acetyloxy group is generally the most inexpensive but the groups can be a glycolic acid derivative group for increasing the transfer efficiency and also a butyryloxy group for increasing the recoloring speed. When the Y group is a hydroxyl group, the dye developer can have a hydrazono type structure as an ordinary azo dye.

Suitable polyhydric phenol moieties are a hydroquinone group, a catechol group, etc., which also can be nuclear substituted with alkyl groups containing from 1 to 3 carbon atoms or halogen atoms. An acylated group capable of forming hydroquinone or catechol in a processing composition can be used as the polyhydric phenol. It is desirable that the polyhydric phenol moiety having silver halide development activity be bonded to the dye portion through an atom, a divalent atomic group, or preferably an alkylene group having 1 to 6 carbon atoms bonded directly to the polyhydric phenol moiety from the standpoint of development activity although such bonding is not essential in this invention.

Specific examples of dye developers used in this invention are illustrated below.

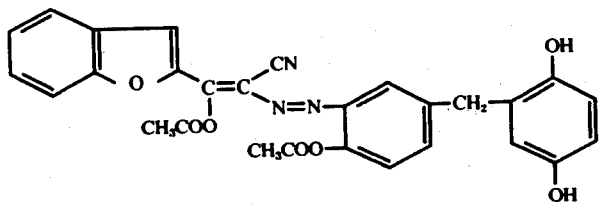
(1)
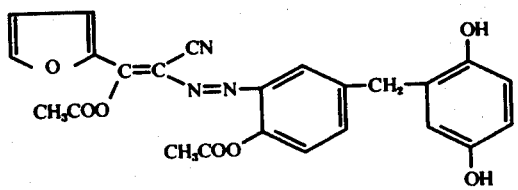
(2)
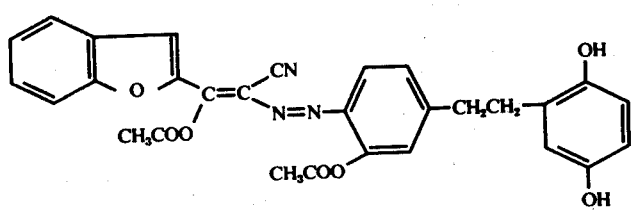
(3)
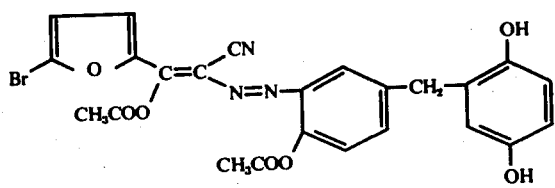
(4)
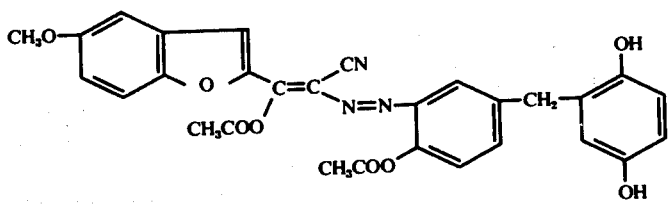
(5)
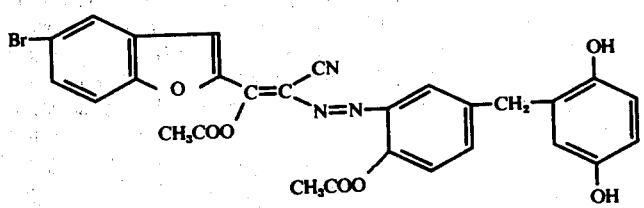
(6)
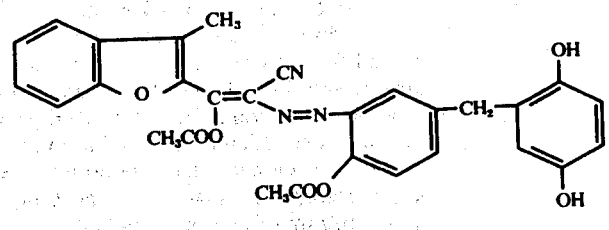
(7)

-continued

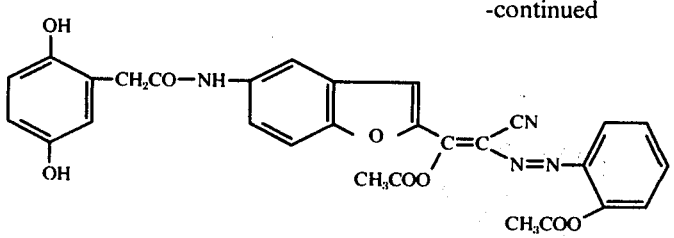
(8)

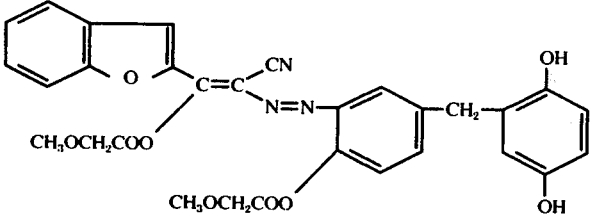
(9)

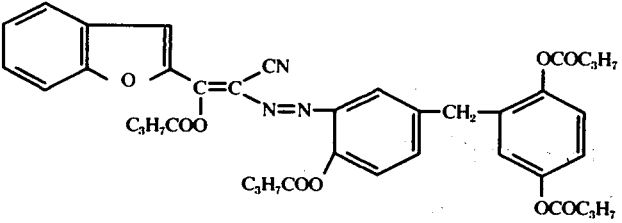
(10)

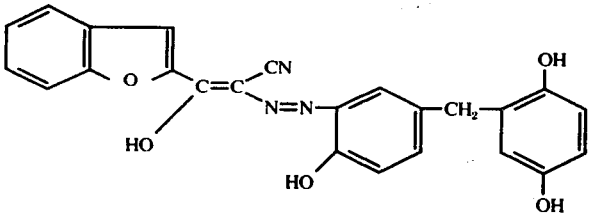
(11)

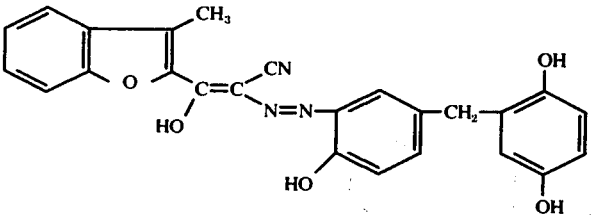
(12)

It is quite important that each of the dye developers has a hydroxyl group or an acyloxy group at the ortho-position to the azo group. The acyloxy group is hydrolyzed by a processing solution having a high pH, whereby the dye developer having a hydroxyl group diffuses. The hydroxyl group (or an acyloxy group) at the ortho-position to the azo group has the remarkable effect of shifting the hue of the transferred image to a desirable wave length side.

Figure 2:
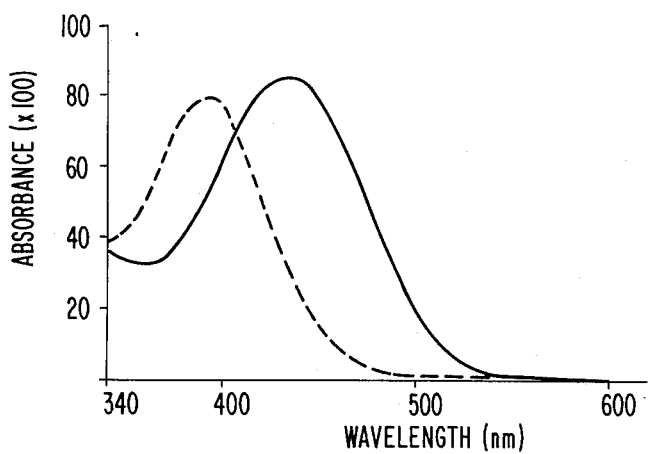
FIG. 2 shows the effect on the spectral absorption of a hydroxyl group in an ortho position to the azo group. The solid line shows the absorbance of Dye Developer 11 in an acetone solution and the dotted line shows the absorbance of a comparison compound, ($\alpha$-[m-Hydroquinonylmethyl)phenylazo]$\beta$-hydroxy-$\beta$-(2-benzofuranyl) acrylonitrile), having no hydroxyl group in an ortho position to the azo group in acetone solution.

That is, the solid line of FIG. 2 of the accompanying drawings shows the spectral absorption curve of an acetone solution of 1.73 mg./100 ml. of Dye Developer 11 of this invention and the dotted line of FIG. 2 shows the spectral absorption curve of an acetone solution of 1.60 mg./100 ml. of a comparison compound, α-[m-(hydroquinonyl)phenylazo]-hydroxy-β-(2-benzofuranylacrylonitrile). From the results shown in FIG. 2, it can be understood that the dye developer of this invention has a more desirable absorption after recoloring in an image-receiving layer and a processing solution as compared with the dye developer described in the specification of U.S. patent application Ser. No. 486,730 filed July 8, 1974.

Figure 3:
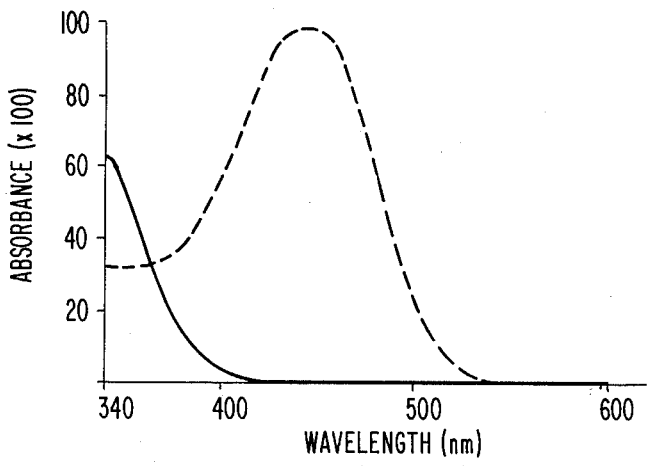
FIG. 3 shows the spectral absorption of Dye Developer 7 (solid line) and Dye Developer 12 (dotted line) in acetone solution.

Furthermore, the hydroxyl group (or an acyloxy group) of the dye developer is converted into a phenoxy anion by dissociation (or hydrolysis) under a high pH and contributes to promote the diffusion of the dye developer and to increase the transfer efficiency. The acyloxy group is for fixing the azo dye in the azo-type tautomer as described above, whereby the temporary shifting to a shorter wave length side can be attained. That is, the solid line of FIG. 1 of the accompanying drawings shows the spectral absorption curve of an ethanol solution of 2.97 mg./100 ml. of Dye Developer 1 and the dotted line shows that of the same solution after addition of one drop of a 1 N aqueous sodiu..n hydroxide solution followed by neutralization with acetic acid. Also, the solid line of FIG. 3 shows the spectral absorption curve of an acetone solution of 2.16 mg/199 ml of Dye Developer 7 and the dotted line shows the spectral absorption curve of an acetone solution of 1.82 mg/100 ml of Dye Developer 12.

The dye developers of this invention can be prepared very advantageously by applying the process for producing azo dyes as described in the specification of U.S. patent application Ser. No. 452,576 filed Mar. 19, 1974. That is, it has been found that, in the aromatic primary amine having a hydroquinone residue in the molecule represented by the formula (II)

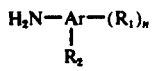
(II)

wherein Ar, $R_1$, $R_2$ and n have the same meaning as in the above-described general formula (I), with Ar or $R_1$ being bonded to a hydroquinone residue directly or through an atom or a divalent group, or a salt thereof, the diazonium salt formed by simultaneously diazotizing the amine portion and oxidizing the hydroquinone portion couples with the coupler having the formula (III)

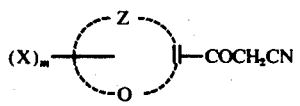
III wherein X, Z and m have the same meaning as in the above-described general formula (I) to afford a yellow azo dye having a quinone residue. The azo-coupling reaction is generally performed at a pH which is preferably not greater than about 9 and the coupler is usually allowed to react after dissolving the coupler in a water-soluble organic solvent such as methanol, ethanol and the like. The above-described azo dye having a quinone residue can also be prepared by diazotizing an amine having a hydroquinone residue protected by an acetyl group, coupling the diazotized product with the coupler (III) shown above, removing the protective group to form an azo dye having a hydroquinone residue, and oxidizing the hydroquinone residue of the resulting azo dye. The above-described process now discovered is superior to the process described immediately above in the points that the production is shorter and simpler and also the yield of the product is higher.

The dye developer of this invention whose absorbance is temporarily shifted to a shorter wave length side can be prepared by acylating the enolic hydroxyl group of the yellow azo dye having the quinone residue thus prepared with an acylating agent preferably, an enol ester such as an isopropenyl carboxylate in the presence of an acid catalyst and then reducing the quinone residue of the acylated dye with 2,5-di-t-butyl-hydroquinone as disclosed in Japanese Pat. No. 42859/1974 with N,N-disubstituted hydroxylamine as described in U.S. Pat. Ser. No. 543,908, Mar. 22, 1974 or with hydrogen in the presence of an appropriate catalyst such as a palladium-carbon catalyst.

Also, the yellow dye developer, whose absorption has not been temporarily shifted to a shorter wave length side and which is included in the dye developers of this invention, can be prepared by reducing the quinone portion of the azo dye having a quinone residue in the manner described above without acylating the enolic hydroxyl group of the azo dye.

These dye developers can be used for the photographic materials of the type where a negative element is stripped from an image-receiving element for observing the image after transfer and further used advantageously for photographic materials of the type where observation of the transferred image is possible without stripping the negative element as described in U.S. patent application Ser. Nos. 476,241 filed June 4, 1974, Ser. No. 498,336, filed Aug. 19, 1974, Ser. No. 498,005, filed Aug. 14, 1974 and U.S. Pat. Nos. 3,415,644; 3,415,645 and 3,415,646. In particular, the non-stripping photographic material of the type where the transferred image is observed from the side opposite to the exposure side is superior to the photographic material of the type where the image is observed from the exposure side since the former does require means in the camera for optical image inversion. In such a photographic material, it is very important for obtaining preferred color separation for the photographic material to be composed of, in succession, an image-receiving layer, a space for spreading a processing solution, a blue-sensitive silver halide emulsion layer, and a hydrophilic colloid layer containing a yellow dye developer and also the photographic material is exposed from the side closer to the layer containing the yellow dye developer. Thus it is particularly significant that the dye developer be of the type whose absorbance is temporarily shifted to the shorter wave length side.

A photosensitive element for color diffusion transfer process contains a silver halide emulsion having associated therewith a dye developer. Depending on the desired color reproduction, a combination of the spectral sensitivity of a silver halide emulsion and the spectral absorption of the dye image is appropriately selected. For reproduction of natural color by the subtractive color photographic process, a photosensitive element comprising at least two combinations each of a silver halide emulsion having a selective spectral sensitivity in a certain wave length region and a compound capable of providing a dye image having a selective spectral absorption at the same wave length region is used. A photosensitive element comprising a combination of a blue-sensitive silver halide emulsion and a compound capable of providing a yellow dye image, a combination of a green-sensitive silver halide emulsion and a compound capable of providing a magenta dye image, and a combination of a red-sensitive silver halide emulsion and a compound capable of providing a cyan dye image is particularly useful. Magenta dye developers as disclosed in U.S. Pat. Nos. 3,307,947 and 3,579,334 and cyan dye developers as disclosed in Japanese Pat. Nos. 139,418/1973 and 16,026/1974 can be used in the photographic element in combination with the yellow dye developers of the present invention. Each combination unit of the silver halide emulsion and the dye developer can be formed as layers by coating the layers in a face-to-face relation in the photosensitive element or can be present as particles thereof in the same layer in the photosensitive element. In a preferred layer structure of the photosensitive element, a blue-sensitive silver halide emulsion layer, a green-sensitive silver halide emulsion layer, and a red-sensitive silver halide emulsion layer are disposed successively as layers from the exposure side and, in particular, in the case of high-sensitive silver halide emulsions containing silver iodide, it is preferred that a yellow filter layer be positioned between the blue-sensitive silver halide emulsion layer and the green-sensitive silver halide emulsion layer. The yellow filter layer contains a yellow colloidal silver dispersion, a dispersion of an oil-soluble yellow dye, an acid dye mordanted to a basic polymer, or a basic dye mordanted to an acid polymer. The silver halide emulsion layers are advantageously separated from each other by an intermediate layer. The intermediate layer prevents the occurence of undesirable interaction between the silver halide emulsion layers having different color sensitivities. The intermediate layer comprises a hydrophilic polymer such as gelatin, polyacrylamide, and a partial hydrolysis product of polyvinyl acetate, a porous polymer formed by a latex of a hydrophilic polymer and a hydrophobic polymer as described in the specification of U.S. Pat. No. 3,625,685, or a polymer whose hydrophilic property is gradually increased by a liquid processing composition, such as calcium alginate as described in the specification of U.S. Pat. No. 3,384,483.

The silver halide emulsion used in this invention is a hydrophilic colloid dispersion of silver chloride, silver bromide, silver chlorobromide, silver iodobromide, silver chloroiodobromide, or a mixture thereof. The halogen composition can be appropriately selected depending on the end-use purposes of the photographic material and the processing conditions employed but a silver iodobromide emulsion or a silver chloroiodobromide emulsion wherein the iodide content is about 1 to 10 mole percent (the chloride content is less than about 30 mole percent) and the rest bromide is particularly preferred. The grain size of the silver halide used can be an ordinary grain size or a fine grain size but a silver halide having a mean grain size ranging from about 0.1 micron to about 2 microns is preferred. Furthermore, depending on the end-use purpose of the photograhic material, a silver halide having uniform grain size is preferred. The crystal form of the silver halide grains can be a cubic system, an octahedral system, or a mixed crystal system.

These silver halide emulsions can be prepared using known conventional methods as described, for example, in P. Glafkides; *Chimie Photographique;* Chapters 18–23, 2nd Edition, Paul Montel, Paris (1957). That is, a soluble silver salt such as silver nitrate and a water-soluble halide such as potassium bromide can be reacted in an aqueous solution of a hydrophilic protective colloid such as gelatin and the growth of the silver halide formed is conducted in the presence of excess halide or in the presence of a silver halide solvent such as ammonia. The silver halide can be prepared using the so-called single jet method, double jet method, or a pAg control double jet method. Soluble salts can be removed from the silver halide emulsion thus formed by washing the cool-set silver halide emulsion with water, by dialysis, by the addition of sedimenting agent such as an anionic polymer or an anionic surface active agent having a sulfone group, a sulfuric acid ester group, or a carboxyl group followed by pH adjustment, or by the use of an acylated protein such as phthaloyl gelatin as a protective colloid followed by a pH adjustment.

It is desirable that the silver halide emulsion used in this invention be chemically sensitized using the natural sensitizers contained in gelatin, a sulfur sensitizer such as sodium thiozulfate or N,N,N'-triethylthiourea e.g., as described in U.S. Pat. Nos. 1,574,944; 2,278,947; 2,440,206; 2,410,689; 3,189,458; 3,415,649, etc., a gold sensitizer such as a complex salt of mono-valent gold and thiocyanate or a complex salt of mono-valent gold and thiosulfate e.g., as described in U.S. Pat. Nos. 2,540,085; 2,597,856; 2,597,905; 2,309,083, etc., a reducing agent such as stannous chloride or hexamethylenetetramine e.g., as described in U.S. Pat. Nos. 2,518,698; 2,419,974; 2,983,610, etc., or a combination of these methods followed by heating. In the present invention, a silver halide emulsion capable of forming a latent image on the surface of the silver halide grains as well as a silver halide emulsion capable of forming a latent image in the silver halide grains as described in the specifications of U.S. Pat. Nos. 2,592,550 and 3,206,313 can be used. A suitable coating amount of the emulsion ranges from about 0.01 $g/m^2$ to 10 $g/m^2$, preferably 0.3 $g/m^2$ to 4 $g/m^2$ (as silver per $m^2$ of the support).

The silver halide emulsion used in this invention can be stabilized using an additive such as 4-hydroxy-6-methyl-1,3,3a,7-tetraazaindene, 5-nitroimidazole, 1-phenyl-5-mercaptotetrazole, 8-chloromercuryl quinoline, benzenesulfinic acid, pyrocatechin, 4-methyl-3-sulfoethylthiazolidine-2-thione, and 4-phenyl-3-sulfoethylthiazolidine-2-thione. Furthermore, an inorganic compound such as a cadmium salt, a mercury salt, or a chloro complex salt of palladium is also useful for the stabilization of the photographic material of this invention. Still further, the silver halide emulsion used in this invention can contain a sensitizing compound such as a polyethylene oxide compound.

The silver halide emulsion used in this invention can have a color sensitivity enlarged, if desired, by a spectral sensitizing dye. Examples of the useful spectral sensitizing dyes are cyanine dyes, merocyanine dyes, holopolar cyanine dyes, styryl dyes, hemicyanine dyes, oxanole dyes, hemioxanoles, etc. Specific examples of useful spectral sensitizers are described in P. Glafkides; *Chimie Photographique;* Chapters 35–41 and F. M. Hamer; *The Cyanine Dyes and Related Compounds;* (Interscience). In particular, cyanines in which the nitrogen atom of the basic heterocyclic ring nucleus is substituted with an aliphatic group (such as an alkyl group) having a hydroxyl group, a carboxyl group, or a sulfo group as described in the specifications of U.S. Pat. Nos. 2,503,776; 3,459,553 and 3,177,210 are particularly useful for the practice of this invention.

The dye developer of this invention is generally dispersed in a hydrophilic colloid as a binder in the following manner. That is, the dye developer is dissolved in an organic solvent and the solution is dispersed as fine droplets in an aqueous solution of a hydrophilic colloid such as gelatin. When the solvent is a volatile solvent such as ethyl acetate, tetrahydrofuran, and methyl ethyl ketone, the solvent can be removed in the drying of the photographic emulsion layers, or using the techniques described in the specifications of U.S. Pat. Nos. 2,801,171 and 2,322,027. When the solvent is one readily soluble in water, such as dimethylformamide and 2-methoxyethanol, the solvent can be removed by water washing as described in the specifications of U.S. Pat. Nos. 2,949,360 and 3,306,027. However, for stabilizing the dispersion of the dye developer and promoting the speed of dye image formation, it is advantageous to incorporate the dye developer in an organic solvent substantially insoluble in water and having a boiling point of higher than about 200° C. Examples of such a high boiling solvent are dibutyl phthalate, tricresyl phosphate, trihexyl phosphate, N,N-diethyl lauramide, etc. To accelerate the dissolution of the dye developer, it is desirable to use the above-described water-soluble or volatile solvent as an auxiliary solvent.

Furthermore, an oleophilic polymer can be used in place of or in addition to the high-boiling organic solvent. In general, for dispersing the dye developer solution as fine droplets, a colloid mill, a high-pressure homogenizer, an ultrasonic emulsifier, etc., can be used and also an anionic surface active agent is preferably used as an emulsification assistant. A suitable amount of the dye developer of this invention ranges from about 0.1 g/m$^2$ to 10 g/m$^2$, preferably 0.3 g/m$^2$ to 4 g/m$^2$ of the support.

The photosensitive element as described above is superposed on an image-receiving element in a face-to-face relation and is generally processed by spreading an alkaline processing solution in a space between the two elements. In this case, the image-receiving element can be stripped off after image transfer or the transferred image can be observed without stripping off the image-receiving element by using a transparent support such as a cellulose triacetate film, a polyethylene terephthalate film, etc., as the support for the image-receiving layer and placing a light reflecting layer between the image-receiving layer and the photosensitive layer as described in the specification of U.S. Pat. No. 3,415,646.

The image-receiving element includes a mordant layer composed of a poly-4-vinylpyridine latex (particularly in polyvinyl alcohol) or polyvinyl pyrrolidone or futher a polymer containing a quaternary ammonium salt as described in the specification of U.S. Pat. No. 3,239,337 and further it is desirable that the image-receiving element is capable of neutralizing the alkali carried in from a liquid processing composition.

The liquid processing composition contains an alkali to provide a pH higher than about 10, preferably higher than 11, sufficient for promoting image-formation comprising the development of the silver halide emulsion layers and the diffusion of the dye developers. After the formation of the transferred image by diffusion is substantially completed, the pH in the photographic film unit is neutralized below about 9, preferably below 8 to substantially stop image-formation and to prevent a change of the tone of the images formed with the passage of time and further suppress the discoloration of the images caused by the high alkali and the occurence of stains of the highlight area. For this purpose, a neutralization layer containing a sufficient amount of an acidic material for neutralizing the alkali contained in the liquid processing composition to the above-described pH value, that is, an acidic material of an area density higher than the equivalent to the alkali contained in the liquid processing composition spread between the two elements, is employed in the photographic film unit. A preferred acidic material is a material containing an acid group (in particular, a carboxylic acid group, a sulfonic acid group, or a precursor capable of providing such an acid group by hydrolysis) having pKa below about 9 and more preferred examples of suitable acidic material are higher fatty acids such as oleic acid as described in the specification of U.S. Pat No. 2,983,606 and a polymeric acidic materials such as acrylic acid polymer, methacrylic acid polymer, or maleic acid polymer, a partial ester of the maleic acid polymer, and the maleic anhydrides polymer as described in the specification of U.S. Pat. No. 3,362,819. Further examples of polymeric acid materials are a copolymer of maleic anhydride and a vinyl monomer such as ethylene, vinyl acetate, vinyl methyl ether, etc., and the n-butyl half ester of the maleic anhydride copolymer, a copolymer of butyl acrylate and acrylic acid, cellulose acetate hydrogen phthalate, etc. The neutralization layer can contain further a polymer such as cellulose nitrate and polyvinyl acetate and a plasticizer as described in the specification of U.S. Pat. No. 3,557,237 in addition to the above described acid material. Furthermore, the neutralization layer can be hardened by cross-linking with a polyfunctional aziridine compound, an epoxy compound, etc.

The neutralization layer can be positioned in the image-receiving element and/or the photosensitive element but it is particularly advantageous to position the neutralization layer between the support for the image-receiving element and the image-receiving layer. Furthermore, the acid material can be used in the photographic film unit in an encapsulated form as described in German OLS No. 2,038,254.

The neutralization layer or the acid material-containing layer preferable is separated from the layer of the liquid processing composition spread between the image-receiving element and the photosensitive element by a neutralization rate controlling layer. The neutralization rate controlling layer contributes to prevent an undesirable reduction in the density of the transferred image due to a too quick reduction of the pH of the processng liquid by the neutralization layer before the development of the desired silver halide emulsion layers and the formation of the transferred images by diffusion are completed delaying the pH reduction until the desired development and transfer are completed.

In a preferred embodiment of this invention, the image-receiving element or portion has a multilayer structure comprising a support having coated thereon a neutralization layer, a neutralization rate controlling layer, and a mordant layer (or image-receiving layer). The neutralization rate controlling layer mainly comprises gelatin, polyvinyl alcohol, polyvinylpropyl ether, polyacrylamide, hydroxypropylmethyl cellulose, isopropyl cellulose, polyvinyl alcohol partial butyral, partially hydrolyzed polyvinyl acetate, or a copolymer a β-hydroxyethyl methacrylate and ethyl acerylate. It is advantageous to harden the above described polymer by crosslinking due to an aldehyde compound such as formaldehyde or an N-methylol compound. It is also preferred that the neutralization rate controlling layer has a thickness of about 2 to 20 microns.

The liquid processing composition used in this invention is a liquid composition containing the necessary components for the development of the silver halide emulsion layers and foormation of transferred dye images by diffusion. The solvent is mainly water, but can contain additionally a hydrophilic solvent such as methanol and 2-methoxyethanol. The liquid processing composition contains an alkaline material in a sufficient amount for neutralizing the acids (e.g., a hydrohalic acid such as hydrobromic acid and a carboxylic acid such as acetic acid) formed during the development and the various steps for the formation of dye images and for maintaining the necessary pH value for development of the silver halide emulsion layers. Examples of suitable alkaline materials are alkali metal hydroxides, such as lithium hydroxide, sodium hydroxide, or potassium hydroxide, alkaline earth metal hydroxide such as calcium hydroxide, amine compounds such as tetramethylammonium hydroxide, diethylamine, and alkaline salts such as sodium carbonate, sodium phosphate, etc. It is more preferred that the processing composition contains an alkali metal hydroxide in an amount sufficient to maintain the pH higher than about 12, preferably higher than 14. Furthermore, preferably the liquid processing composition contains a hydrophilic polymer such as a high-molecular weight polyvinyl alcohol, hydroxyethyl cellulose, sodium carboxymethyl cellulose, etc. These polymers provide a viscosity of higher than 1 poise, preferably 500 to 1000 poises, at room temperature (about 20° to 30° C) to the liquid processing composition for facilitating the uniform spreading of the processing composition in processing and also to form a non-fluid film when the aqueous medium diffuses from the spread liquid processing composition into the photosensitive element and the image-receiving element and thus the processing composition is concentrated assisting the unification of film unit after processing. The polymer film can prevent the transfer of coloring components further to the image-receiving layer after the formation of the transferred dye images by diffusion is substantially completed, whereby a change in the dye images can be prevented.

It is sometimes advantageous that the liquid processing composition contains, in addition to the above-described components, a light absorbing material such as carbon black and a desensitizer as described in the specification of U.S. Pat. No. 3,579,333 for preventing the silver halide emulsion layers from being fogged by ambient light during processing, e.g., outside a camera.

In a color diffusion transfer process, the development process preferably is carried out in the presence of a diffusible onium compound. Examples of such an onium compound are quaternary ammonium compounds, quaternary sulfonium compounds, and quaternary phosphonium compounds. Specific examples of particularly useful onium compounds are 1-benzyl-2-picolinium bromide, 1-(3-bromopropyl)-2-picolinium-p-toluene sulfonic acid, 1-phenthyl-2-picolinium bromide, 2,4-dimethyl-1-phenethyl-pyridinium bromide, α-picoline-β-naphthoylmethyl bromide, N,N-diethyl-piperidinium bromide, phenethylphosphonium bromide, dodecyldimethylsulfonium-p-toluene sulfonate, etc. The onium compound desirably is incorporated in the processing composition. A most preferable amount of the onium compound employed in the processing composition is about 2 to 15% by weight of the total amount of the processing composition. By conducting the development in the presence of the onium compound, the quality of the transferred dye images is remarkably increased. Other examples of suitable onium compounds are described in the specification of U.S. Pat. Nos. 3,411,904 and 3,173,786 together with their uses. Moreover, the liquid processing composition can contain a development inhibitor such as benzotriazoie.

The preparations of the compounds of this invention and the use of the compounds of this invention in photographic materials will be explained by the following examples. Unless otherwise indicated herein all parts, percents, ratios and the like are by weight.

EXAMPLE 1

Preparation of Compound 1:

a. Preparation of 3-Oxo-3-(2'-benzofuranyl)-2-[(2''-hydroxy-5''-quinonylmethyl)phenylhydrazono]propionitrile:

A mixture of 19.2 g. of 3-amino-2'',4,5''-trihydroxydiphenyl methane, 1 liter of ice-water, 60 ml. of 35% hydrochloric acid, and 3 ml. of octyl alcohol (as a defoaming agent) was stirred well to form a solution and the solution was cooled to 0° C. To the stirred solution was added dropwise 100 ml. of an aqueous solution of 17.5 g. of sodium nitrite over a period of 15 minutes at 0° C. After stirring the mixture for 80 minutes, 1.0 g. of sulfamic acid and then 100 g. of sodium acetate were added to the mixture. Then, a mixture of 1 liter of an ethanol solution of 15.0 g. of 2-(2'-cyanoacetyl)coumarone and 20 ml. of an aqueous solution of 4.0 g. of sodium hydroxide was added to the diazonium salt solution prepared above. The crystals thus precipitated were recovered by filtration and recrystallized from 1,2-dichloroethane to provide 17.2 g. of orange crystals of the aforesaid compound having a melting point of 204–205° C.

b. Acylation of the Enol:

In 300 ml. of 1,2-dichloroethane were dissolved 17.2 g. of the azo dye prepared in procedure (a), 300 ml. of isopropenyl acetate, and 1 ml. of concentrated (95%) sulfuric acid and the solution was refluxed on a steam bath. The reaction mixture was washed with water and then treated with sodium sulfate and activated carbon. When the solution was filtered and concentrated, crystals precipitated, which were collected by filtration, washed with ethyl acetate and dried with air to provide 10.19 g. of α-[(2-acetoxy-5-quinonylmethyl)phenylazo]- -acetoxy- -(2-benzofuranyl)acrylonitrile having a melting point of 187–188° C.

c. Preparation of Compound 1:

In 100 ml. of 1,2-dichloroethane was dissolved 7.0 g. of the compound prepared in procedure (b) and then 5.0 g. of 2,5-di-t-butylhydroquinone was added to the solution. After being stirred for 20 minutes, the mixture was concentrated. When ethyl acetate was added to the concentrate, crystals precipitated, which were collected by filtration, washed with benzene, and recrystallized from acetone to provide 6.0 g. of Compound 1 having a melting point of 211–213° C.

EXAMPLE 2

Preparation of Compound 7:

a. Preparation of 3-Oxo-3-[2'-(3'-methyl)benzofuranyl]-2-[(2''-hydroxy-5''-quinonylmethyl)phenylhydrazono]propionitrile:

In the same manner as in procedure (a) of Example 1, a diazo solution was prepared from 4.6 g. of 3-amino-2',4,5-trihydroxy-diphenylmethane and the solution was coupled with 4.0 g. of 2-(2'-cyanoacetyl)-3-methylcoumarone to provide 2.8 g. of the aforesaid compound having a melting point of 205°–208° C. (recrystallized from ethyl acetate).

b. Acylation of the Enol:

In the same manner as in procedure (b) of Example 1, 1.5 g. of α-[(2-acetoxy-5-quinonylmethyl)-phenylazo]-β-acetoxy β-[2'-(3'-methylbenzofuranyl)-]acrylonitrile was obtained from 2 g. of the compound prepared in procedure (a). The product recrystallized from ethyl acetate had a melting point of 176°–179° ↺.

c. Preparation of Compound 7:

In the same manner as in procedure (c) of Example 1, 1.2 g. of the compound prepared in procedure (b) was reduced with 0.6 g. of 2,5-di-t-butylhydroquinone and then the product was recrystallized from ethyl acetate to provide 1.0 g. of compound 7 having melting point of 213°–215° C.

EXAMPLE 3

Preparation of Compound 11:

In 100 ml. of 1,2-dichloroethane was dissolved 1.0 g. of the compound prepared in procedure (a) of Example 1 and after adding to the solution 2.0 ml. of N,N-diethylhydroxylamine, the mixture was allowed to stand for 15 minutes. When 100 ml. of water was added to the mixture, crystals were precipitated, which were recovered by filtration and recrystallized from ethyl acetate to provide 0.7 g. of Compound 11 having a melting point of 227°–230° C.

EXAMPLE 4

Photosensitive Element I was prepared by coating, in succession, on a cellulose triacetate film having a gelatin subbing layer the following layers:

1. Yellow Dye Developer Layer:

After dissolving 1 part of Compound 1 in a mixture of 1 part of N,N-diethyllaurylamide and 4 parts of cyclohexanone, the solution was dispersed by emulsification in an aqueous solution of gelatin using sodium n-dodecylbenzenesulfonate as a dispersing agent and then the emulsion obtained was coated at a coverage of 1.4 g./m$^2$ of the dye developer, 2.4 g/m$^2$ of gelatin, and 1.4 g/m$^2$ of N-N-diethyllaurylamide.

2. Blue-Sensitive Emulsion Layer:

A blue-sensitive silver iodobromide emulsion (containing 2 mole% of silver iodide) was coated on the yellow dye developer layer at a coverage of 3.5 g/m$^2$ of silver and 4.0 g/m$^2$ of gelatin.

3. Protective Layer:

After dissolving 1 part of 4-methylphenylhydroquinone in 1 part of ethyl acetate containing 1.5 parts of tri-o-cresyl phosphate, the solution was dispersed by emulsification in an aqueous solution of gelatin using sodium n-dodecylbenzene sulfonate and the emulsion prepared was coated at a coverage of 0.20 g/m$^2$ of 4'-methylphenylhydroquinone, 0.6 g/m$^2$ of gelatin, and 0.20 g/m$^2$ of tri-o-cresyl phosphate. In this case mucochloric acid was used as a hardening agent.

Also, as a comparison sample to Photosensitive Element I, Photosensitive Element II was prepared in the same way as above except that the following layer was employed as the yellow dye developer layer.

Yellow Dye Developer Layer:

After dissolving 1 part of 1-phenyl-3-(N-n-hexylcarboxyamide)-4-[4-(2-hydroquinonylethyl)phenylazo]-5-hydrazone (Comparison Dye Developer-1) in a mixture of 2.5 parts of N,N-diethyllaurylamide and 2.5 parts of cyclohexanone, the solution was dispersed by emulsification in an aqueous solution of gelatin using sodium n-dodecylbenzenesulfonate and the emulsion was coated at a coverage of 1.4 g/m$^2$ of the dye developer, 2.4 g/m$^2$ of gelatin, and 3.5 g/m$^2$ of N,N-diethyl laurylamide.

Furthermore, as another comparison sample to Photosensitive Element I, Photosensitive Element III was prepared in the same way as the preparation of Photosensitive Element I except that the following layer was employed as the yellow dye developer layer.

Yellow Dye Developer Layer:

After dissolving 1 part of α-[p-(2-hydroquinonylethyl)phenyl-azo]-β-acetoxy-β-(2'-benzofuranyl)acrylonitrile (Comparison Dye Developer -2) in a mixture of 1.5 parts of N,N-diethyllaurylamide and 4 parts of cyclohexanone, the solution was dispersed by emulsification is an aqueous solution of gelatin using sodium n-dodecylbenzenesulfonate and the emulsion was coated at a coverage of 1.4 g/m$^2$ of the dye developer, 2.4 g/m$^2$ of gelatin, and 2.1 g/m$^2$ of N,N-diethyllaurylamide.

Then, an image-receiving element was prepared by coating, in succession, on a transparent polyethylene film the following layers:

1. Acid Polymer Layer:

A 20% methyl ethyl ketone solution of the butyl half ester of 1 : 1 molar ratio copolymer of maleic anhydride and vinyl methyl ether (having a means molecular weight of about 100,000) was coated at a dry thickness of 20 microns.

2. Neutralization Rate Control Layer:

In a mixture of 3 parts of acetone and 1 part of water was dissolved 1 part of 2-hydroxyethyl methacrylate and the solution was coated at a dry thickness of .7 microns.

3. Image-Receiving Layer:

After dissolving 1 part of poly-4-vinylpyridine, 2 parts of polyvinyl alcohol (saponification degree: 98%, and polymerization degree: 1800), and 0.05 part of 1-phenyl-5-mercaptotetrazole in 150 parts of water containing 0.5 part of glacial acetic acid, the solution was coated at a coverage of 3.2 g/m$^2$ of poly-4-vinylpyridine, 3.2 g/m$^2$ of polyvinyl alcohol, and 0.16 g/m$^2$ of 1-phenyl-5-mercaptotetrazole.

Each of Photographic Elements I, II, and III was exposed through an optical wedge to a tungsten light of a color temperature of 2854° K at 20 C. M. S. from the support side and after superposing it on the image-receiving element. A processing solution having the following composition was spread therebetween at 1.5 ml. per 100 cm$^2$ of the image receiving element to conduct the development transfer

| | | |
|---|---|---|
| Water | 100 | ml |
| Potassium Hydroxide | 11.2 | g |
| Hydroxyethyl Cellulose | 4.0 | g |
| Benzotriazole | 3.5 | g |
| Potassium Thiosulfate | 0.5 | g |
| Lithium Nitrate | 0.5 | g |
| N-Benzyl-α-picolinium Bromide | 2.3 | g |

After conducting the development for about 1 minute, the image-receiving element was stripped off and washed sufficiently with water. A yellow dye image was transferred to the image-receiving element according to the exposure amount.

The transmission density of the transferred yellow dye was measured using a blue filter and the maximum image density ($D_{max}$) and the minimum image density ($D_{min}$) were 1.24 and 0.29 respectively for Photosensitive Element I and were 0.90 and 0.10 for Photosensitive Element II.

Figure 4:
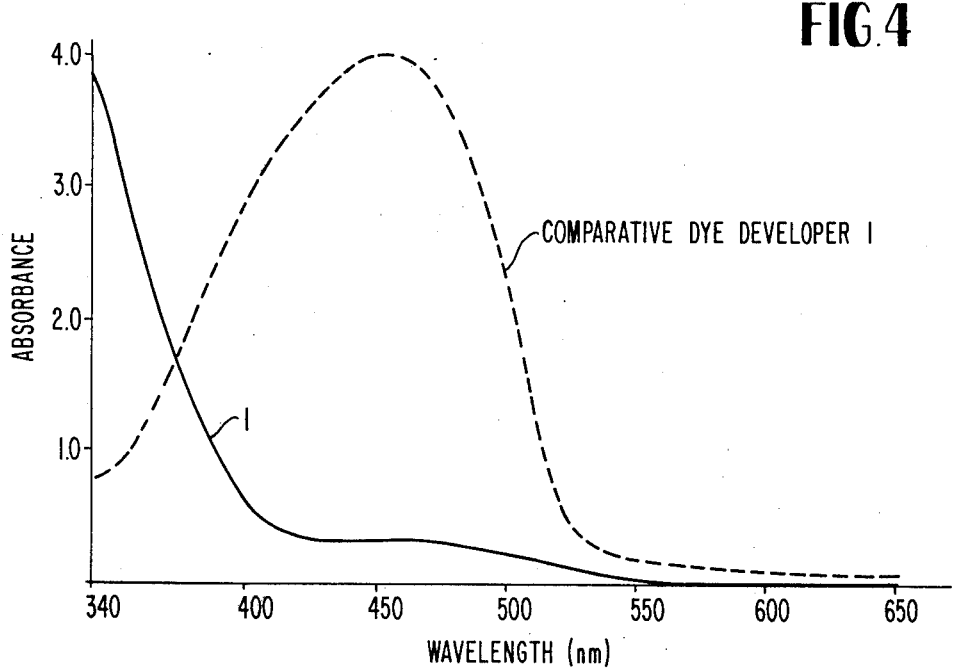
FIG. 4 shows the spectral absorption of a dye developer layer containing Dye Developer 1 and that of Comparative Dye Developer 1 in terms of transmission density.

Each of the fresh Photosensitive Elements I and II was exposed as above from the opposite side to the support and subjected to the same development procedure as above. Then, by investigating the degree of the reduction in sensitivity in the case of exposing the photosensitive element from the support side on comparing the case of exposing from the opposite side to the support, the $-\Delta \log E$ was 0.2 for Photosensitive Element I, while it was 2.4 for Photosensitive Element II and thus the degree of the reduction in sensitivity of Photosensitive Element I was less than that of Photosensitive Element II. Also, for comparing the absorption by the dye developer in the photosensitive element before processing, a sample was prepared by coating on a transparent cellulose triacetate film having a gelatin subbing layer each of the aforesaid dye developer layers only and the spectral absorption of the sample was measured for the transmission density. The results obtained are shown in FIG. 4 of the accompanying drawings. As is clear from the results, in the case of using Compound 1, the absorption shifted to a shorter wave length side as compared with the case of using Comparison Dye Developer-1 and the spectral sensitivity of the blue-sensitive silver halide emulsion associated therewith was not as degraded.

Figure 5:
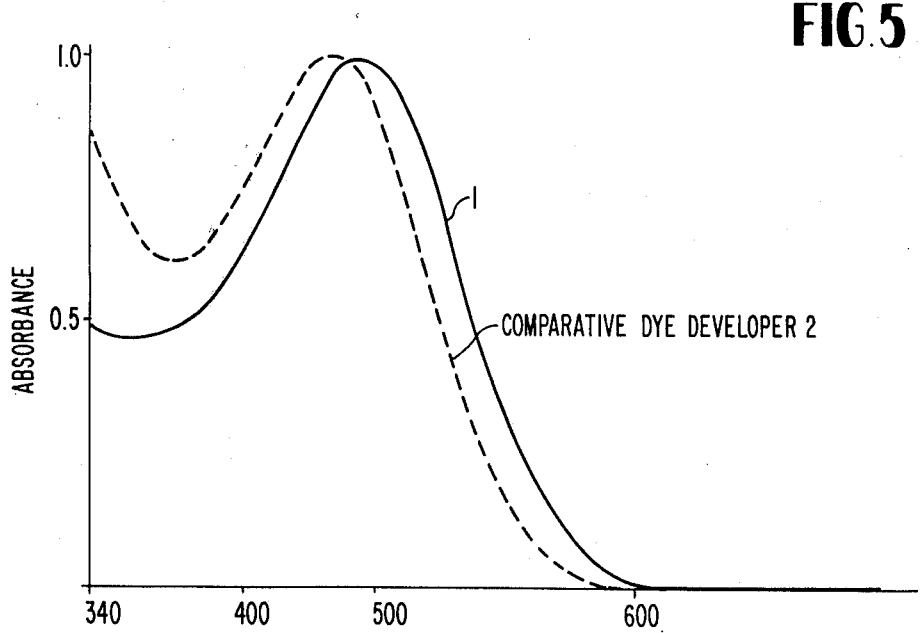
FIG. 5 compares the absorbance of Dye Developer 1 after transfer with that of Comparison Dye Developer 2 after transfer.

The spectral absorption of the dye image in the case of transferring the dye developer in Photosensitive Element I to the image-receiving element at a processing period of 35 seconds was measured for the transmission density and the results obtained are shown in FIG. 5 together with the results obtained by applying the same processing to Photosensitive Element III for 45 seconds. As is clear from the results, the absorption of the transferred dye image in Photosensitive Element I shifted to a shorter wave length side as compared with the case of using Photosensitive Element III.

When the above-described processing was applied to Photosensitive Elements I and III, the ratio (mole ratio) of the amount of the transferred dye to the coated amount of the photosensitive element was 14% for Photosensitive Element I and 20% for Photosensitive Element III at a processing period of 1 minute. Thus, the dye developer used in Photosensitive Element I was confirmed to be superior to the compound used in Photosensitive Element III in transfer efficiency. Also, in the case of dispersing the dye developer, 30 minutes at 80° C. were required to dissolve the dye developer used in Photosensitive Element I in the mixture of N,N-diethyllaurylamide and cyclohexanone at the concentration as described above, while one hour at 140° C. was required in the case of the compound used in Photosensitive Element III. Furthermore, in the case of dispersing the dye developer used in Photosensitive Element I, the amount of N,N-diethyllaurylamide used for the dispersion thereof was confirmed to be less than that in the case of dispersing the compound used in Photosensitive Element III and further the temperature required for dissolving the dye developer for Photosensitive Element I was confirmed to be lower and the time required for dissolving it was confirmed to be shorter than the temperature and time required in the case of using the compound for Photosensitive Element III.

EXAMPLE 5

A photosensitive element was prepared by coating, in succession, on a cellulose triacetate film having a gelatin subbing layer the following layers:

1. Yellow Dye Developer Layer:

After dissolving 1 part of Compound 5 in a mixture of 1 part of N,N-diethyllaurylamide and 4 parts of cyclohexanone, the solution was dispersed by emulsification in an aqueous solution of gelatin using sodium n-dodecylbenzenesulfonate and the emulsion was coated at a coverage of 1.5 g/m² of the dye developer, 1.7 g/m² of gelatin, and 1.5 g/m² of N,N-diethyllaurylamide.

2. Blue-Sensitive Emulsion Layer:

A blue-sensitive silver iodobromide emulsion (containing 2 mole% of silver iodide) was coated at a coverage of 2.3 g/m² of silver and 1.7 g/m² of gelatin.

3. Intermediate Layer:

A colloidal silver solution was coated at a coverage of 0.3 g/m² of silver and 3.5 g/m² of gelatin.

4. Magenta Dye Developer Layer:

After dissolving 1 part of 4-methoxyethoxy-2[4-(2-hydroquinonylethyl)phenylazo]naphthalene-1-acetate in a mixture of 1 part of diethyllaurylamide and 4 parts of cyclohexanone, the solution was dispersed by emulsification in an aqueous solution of gelatin using sodium n-dodecylbenzenesulfonate and the emulsion was coated at a coverage of 1.0 g/m² of the dye developer, 1.3 g/m² of gelatin, and 1.0 g/m² of N,N-diethyllaurylamide.

5. Green-Sensitive Emulsion Layer:

A green-sensitive silver iodobromide emulsion (containing 2 mole% of silver iodide and spectrally sensitized with 3,3', 9-triethyl-5,5'-diphenyloxacarbocyanine bromide) was coated at a coverage of 1.0 g/m² of silver and 0.8 g/m² of gelatin.

6. Intermediate Layer:

A gelatin solution was coated at a coverage of 3.0 g/m² of gelatin.

7. Cyan Dye Developer Layer:

After dissolving 1 part of 1-(N-carbophenoxy-N-γ-hydroquinonylpropylamino)-4-γ-hydroquinonylpropylamino-5,8-dihydroxy-9,10-anthraquinone in a mixture of 2 parts of N,N-diethyllaurylamide and 4 parts of methylcyclohexanone, the solution was dispersed by emulsification is an aqueous solution of gelatin using sodium n-dodecylbenzenesulfonate and the emulsion was coated at a coverage of 0.5 g/m² of the dye developer, 1.2 g/m² of gelatin, and 0.5 g/m² of N,N-diethyllaurylamide.

8. Red-Sensitive Emulsion Layer:

A red-sensitive silver iodobromide emulsion (containing 2 mole% of silver iodide and spectrally sensitized with 3,3',9-triethyl-5,5'-dichlorocarbocyanine iodide) coated at a coverage of 0.50 g/m² of silver and 0.37 g/m² of gelatin.

9. Protective Layer:

After dissolving 1 part of 4'-methylphenylhydroquinone in a mixture of 1 part of tri-o-cresyl phosphate and 1.5 parts of ethyl acetate, the solution was dispersed by emulsification in an aqueous solution of gelatin using sodium n-dodecylbenzenesulfonate and the emulsion was coated at a coverage of 0.45 g/m² of 4'-methylphenylhydroquinone, 1.3 g/m² of gelatin, and 0.45 g/m² of tri-o-cresyl phosphate. In this case, mucochloric acid was used as the hardening agent.

Then, an image-receiving element was prepared by coating, in succession, on a transparent polyethylene film the following layers.

1. Acid Polymer Layer:

A 20% methyl ethyl ketone solution of the butyl half ester of a 1 : 1 molar ratio copolymer of maleic anhydride and vinyl methyl ether (having a mean molecular weight of about 100,000) was coated at a dry thickness of 40 microns.

2. Neutralization Rate Control Layer:

After dissolving 1 part of 2-hydroxyethyl methacrylate in a mixture of 3 parts of acetone and 1 part of water, the solution was coated at a dry thickness of 14 microns.

3. Image-Receiving Layer:

Same as the image-receiving layer in Example 1.

The photosensitive element thus prepared was exposed from the support side to each of red, green, and blue lights through an optical wedge and then transfer development was carried out by spreading a processing liquid having the following composition between the photosensitive element and the image-receiving element at a rate of 1.0 ml. per 100 cm² of the image-receiving element with the elements being in a superposed relationship.

| Processing Composition: | | |
|---|---|---|
| Water | 100 | ml |
| Potassium Hydroxide | 11.2 | g |
| Hydroxylethyl Cellulose | 3.5 | g |
| Benzotriazole | 1.5 | g |
| N-Phenethyl-α-picolinium Bromide | 2.0 | g |
| Titanium Dioxide | 50 | g |

After a few minutes after the development was begun, the appearance of red, green, and blue images could be observed from the support side without stripping off the image-receiving element.

While the invention has been described in detail and with reference to specific embodiments thereof, it will be apparent to one skilled in the art that various changes and modifications can be made therein without departing from the sprit and scope thereof.

What is claimed is:

1. A light-sensitive material for the diffusion transfer process comprising a support having coated thereon a blue-sensitive silver halide emulsion and an associated yellow dye developer represented by the following formula (I)

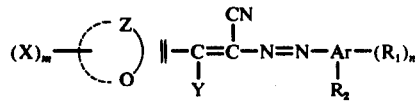

wherein X represents a hydrogen atom, a halogen atom, a nitro group, a hydroxyl group, an alkyl group having 1 to 4 carbon atoms, or an acylamino group having 1 to 4 carbon atoms; Z represents an atomic group necessary for completing a furan ring or benzofuran ring; Y represents a hydroxyl group, an acyloxy group having 1 to 4 carbon atoms or an alkoxyacyloxy group having 2 to 4 carbon atoms; Ar represents an aromatic ring $R_1$ represents a hydrogen atom, a halogen atom, an acyl group having 1 to 4 carbon atoms, or an alkyl group having 1 to 5 carbon atoms; $R_2$ represents a hydroxyl group, an acyloxy group having 1 to 4 carbon atoms, or an alkoxyacyloxy group having 2 to 4 carbon atoms; $R_2$ being at the ortho-position to the azo group; and m and n each represents an integer of 1 to 4; at least one of said Z and Ar being bonded directly or through an atom or divalent group to a polyhydric phenol moiety having a silver halide development activity.

2. The light-sensitive material as claimed in claim 1 wherein said yellow dye developer is positioned at the exposure side to said blue-sensitive silver halide emulsion layer.

3. The light-sensitive material as claimed in claim 1, wherein said blue-sensitive silver halide emulsion and the said yellow dye developer are present in the same layer and said blue-sensitive silver halide emulsion is capable of being spectrally sensitized.

4. The light-sensitive material as claimed in claim 1, further including a container retaining a processing solution for the light-sensitive material and containing a light-reflecting agent.

5. The light-sensitive material as claimed in claim 4, wherein said light-reflecting agent is titanium dioxide.

6. The light-sensitive material as claimed in claim 6, further including an image-receiving element for the dye images transferred on development of said light-sensitive material, said image-receiving element including a mordant layer with a neutralizing rate controlling layer and a neutralizing layer on the side of said mordant layer opposite said light-sensitive silver halide emulsion layer.

7. The light-sensitive material as claimed in claim 6, wherein the mordanting agent has a poly-4-vinylpyridine structure.

8. The light-sensitive material as claimed in claim 1, wherein the silver halide emulsion layer is shielded from light with a light-intercepting agent so that the material can be processed outside a camera in the light.

9. The light-sensitive material as claimed in claim 8, wherein the light-intercepting agent is carbon powder.

10. The light-sensitive material as claimed in claim 1, wherein said yellow dye developer is α-(2-acetoxy-5-hydroquinonylmethylphenylazo)-β-acetoxy-β-(2'-benzofuranyl)acrylonitrile, α-(2-acetoxy-5-hydroquinonylmethylphenylazo)-β-acetoxy-β-(3'-methyl-2'-benzofuranyl)acrylonitrile, α-(2-hydroxy-5-hydroquinonylmethylphenylazo-β-(2'-benzofuranyl)-β-hydroxyacrylonitrile, or α-2-hydroxy-5-hydroquinonylmethylphenylazo)-β-(3'-methyl-2'-benzofuranyl)-β-hydroxyacrylonitrile.

11. The light-sensitive material as claimed in claim 1, further including a green-sensitive silver halide emulsion and an associated magenta dye developer and a red-sensitive silver halide emulsion and an associated cyan dye developer.

12. The light-sensitive material as claimed in claim 1, wherein said halogen atom is a chlorine atom or a bromine atom, wherein said alkyl group having 1 to 4 carbon atoms is a methyl group, an ethyl group, a propyl group, an isopropyl group, a butyl group, a sec-butyl group or a t-butyl group, wherein said acylamino group having 1 to 4 carbon atoms is an acetylamino group, a propionylamino group, or a butyrylamino group, wherein said acyloxy group having 1 to 4 carbon atoms is an acetyloxy group, a propionyloxy group or a butyryloxy group, wherein said alkoxyacyloxy group having 2 to 4 carbon atoms is a methoxyacetyloxy group, wherein said aromatic ring for Ar is a benzene ring or a naphthalene ring, wherein said alkyl group having 1 to 5 carbon atoms is a methyl group, an ethyl group, a propyl group, an isopropyl group, a butyl group, an isobutyl group, a sec-butyl group, a t-butyl group, a sec-amyl group, or a t-amyl group, wherein said polyhydric phenol moiety is a hydroquinonyl group, a 2,5-dihydroxyphenyl group, an ortho-dihydroxyphenyl group, or an acylated derivative thereof and wherein said atom or divalent group is —S—, —NH-CO—, $-(CH_2)_p-S-(CH_2)_q-$ wherein p and q each represent 0 or a positive integer and p + q is less than 6, $-(CH_2)_p-(SO_2-(CH_2)_q-$ wherein p and q each have the same meaning as defined above and an alkylene group containing 1 to 6 carbon atoms.

* * * * *